United States Patent
Hachimura et al.

(10) Patent No.: US 8,226,937 B2
(45) Date of Patent: Jul. 24, 2012

(54) AGENTS FOR PROMOTING IGA PRODUCTION

(75) Inventors: Satoshi Hachimura, Tokyo (JP); Hiroki Kanzato, Sagamihara (JP); Shigeru Fujiwara, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 13/208,597

(22) Filed: Aug. 12, 2011

(65) Prior Publication Data

US 2011/0300118 A1  Dec. 8, 2011

Related U.S. Application Data

(60) Division of application No. 12/487,978, filed on Jun. 19, 2009, now abandoned, which is a continuation of application No. PCT/JP2007/074321, filed on Dec. 18, 2007.

(30) Foreign Application Priority Data

Dec. 21, 2006 (JP) ................................ 2006-344233

(51) Int. Cl.
*A61K 39/02* (2006.01)

(52) U.S. Cl. .................................................. 424/93.45

(58) Field of Classification Search ........................ None
See application file for complete search history.

(56) References Cited

U.S. PATENT DOCUMENTS

| | | | |
|---|---|---|---|
| 5,707,854 A | 1/1998 | Saito et al. | |
| 2003/0215429 A1 | 11/2003 | De Simone | |
| 2004/0009490 A1 | 1/2004 | Glenn et al. | |
| 2004/0115179 A1 | 6/2004 | Liu et al. | |
| 2004/0208863 A1 | 10/2004 | Versalovic et al. | |
| 2005/0214270 A1 | 9/2005 | Yamamoto et al. | |
| 2008/0166787 A1 | 7/2008 | Fujiwara et al. | |
| 2010/0040735 A1 | 2/2010 | Fujiwara et al. | |

FOREIGN PATENT DOCUMENTS

| | | |
|---|---|---|
| EP | 1 555 028 A1 | 7/2005 |
| EP | 1854468 A1 | 11/2007 |
| JP | 7-265064 A | 10/1995 |
| JP | 10-229841 A | 9/1998 |
| JP | 10-309178 A | 11/1998 |
| JP | 2002-306125 A | 10/2002 |
| JP | 2004-26729 A | 1/2004 |
| JP | 2004-277381 A | 10/2004 |
| WO | WO 99/42568 A1 | 8/1999 |
| WO | WO 03045405 A2 | 6/2003 |
| WO | WO 2004/076615 A2 | 9/2004 |
| WO | WO 2006/073145 A1 | 7/2006 |
| WO | WO 2006/093313 A1 | 9/2006 |

OTHER PUBLICATIONS

Michalek et al. (Mol. Immunol., 20:1009-1018, 1983, abstract only).*
Holmgren et al. (Nat. Med. Suppl., 11:545-553, 2005).*
Yamamoto et al. ( Int. J. Oral. Med. Sci., 1:83-89, 2003).*
Chinese First Office Action, Appl. No. 200780051609.X, May 18, 2011, pp. 1-5 (w/ English language translation).
Extended European Search Report dated Dec. 30, 2010 for Application No. 07850807.4.
Geng, F., "New Probiotics—Effects of Lactoamilovorin upon Piglets," Scientific Information of Animal Husbandry Veterinary Medicine, 2001, vol. 4.
Gorbach, S. L., "Probiotics and Gastrointestinal Health," American Journal of Gastroeology, vol. 95, No. 1, 2000, suppl. 1, pp. S2-S4.
JPO International Search Report, Appl. No. PCT/JP2007/074321, Jan. 29, 2008.
Maassen, C.B.M. et al., "Strain-dependent induction of cytokine profiles in the gut by orally administered *Lactobacillus* strains," Vaccine, vol. 18, No. 23, 2000, pp. 2613-2623.
Makras et al., "Kinetic analysis of the antibacterial activity of probiotic *lactobacilli* towards *Salmonella enterica* serovar *Typhimurium* reveals a role for lactic acid and other inhibitory compounds", Research in Microbiol., vol. 157, pp. 241-247, Apr. 2006, XP002614633.
Perdigon, G. et al., "Study of the Possible Mechanisms Involved in the Mucosal Immune System Activation by Lactic Acid Bacteria," Journal of Dairy Science, vol. 82, No. 6, 1999, pp. 1108-1114.
Song, Y. L. et al., "Rapid identification of 11 human intestinal *Lactobacillus* species by multiplex PCR assays using group- and species-specific primers derived from the 16S-23S rRNA intergenic spacer region and its flanking 23S rRNA," FEMs Microbiology Letters, vol. 187, 2000, pp. 167-173.
Vietnamese Office Action, Appl. No. 1-2009-01551, Jul. 28, 2011, pp. 1-2 (w/ English translation).
Akdis, M. et al., "T helper (Th) 2 predominance in atopic diseases is due to preferential apoptosis of circulating memory/effector Th1 cells," The FASEB Journal, 2003, vo. 17, pp. 1026-1035.
Boirivant, M. et al., "*Lamina propria* T cells in Crohn's disease and other gastrointestinal inflammation show defective CD2 pathway-induced apoptosis," Gastroenterology, Mar. 1999, vol. 116, No. 3, p. 557 (Abstract only).

(Continued)

*Primary Examiner* — Nita M Minnifield
*Assistant Examiner* — Brian J Gangle
(74) *Attorney, Agent, or Firm* — Birch, Stewart, Kolasch & Birch, LLP

(57) ABSTRACT

The present invention provides *Lactobacillus* bacteria which enhance the functional of Peyer's patch and promote IgA production and which have a characteristics of localizing on human intestine as well as an agent for promoting IgA production. The present invention is directed to an agent for promoting IgA production containing *Lactobacillus amylovorus* cells, especially *Lactobacillus amylovorus* CP1750 (FERM BP-10532) as an active ingredient.

5 Claims, 1 Drawing Sheet

OTHER PUBLICATIONS

Carol et al., "Certain Strains of *Lactobacillus* can overcome resistance to apoptosis in T lymphocytes from patients with Crohn's disease," Inflammatory Bowel Diseases, vol. 9, No. 7, Supplement 1, Mar. 2003, p. S34.
EPO Extended European Search Report, Appl. No. 06728662.5, Jan. 11, 2012.
Fedorak, R. N. et al., "Probiotics and the Management of Inflammatory Bowel Disease," InFlamm. Bowel Dis., May 20, 2004, vol. 10, No. 3, pp. 286-299.
Guerra, F. et al., "TH2 lymphocytes from atopic patients treated with immunotherapy undergo rapid apoptosis after culture with specific allergens," J. Allergy Clin. Immunol., Apr. 2001, vol. 107, No. 4, pp. 647-653.
Ina, K. et al., "Resistance of Crohn's Disease T Cells to Multiple Apoptotic Signals Is Associated with a Bcl-2/Bax Mucosal Imbalance," The Journal of Immunology, 1999, vol. 163, pp. 1081-1090.
International Preliminary Report on Patentability, Appl. No. PCT/JP2006/304243, May 30, 2007 (w/ English translation).
International Search Report dated Jun. 13, 2006 in International Application No. PCT/JP2006/304243.
Ishida, Y. et al., "Clinical Effects of *Lactobacillus acidophilus* Strain L-92 on Perennial Allergic Rhinitis: A Double-Blind, Placebo-Controlled Study," Journal of Dairy Science, 2005, vol. 88, No. 2, pp. 527-533.
Ishida, Y. et al., "Decrease in Ovalbumin Specific IgE of Mice Serum after Oral Uptake of Lactic Acid Bacteria," Biosci. Biotechnol. Biochem., 2003, vol. 67, No. 5, pp. 951-957.
Ishida, Y. et al., "Development of Soft Drinks Supplemented with Functional Lactobacillus Strain L-92," Japan Food Science, 2004, vol. 43, No. 2, pp. 29-33 (w/ English translation).
Japanese Office Action, dated Dec. 20, 2011, for Japanese Application No. 2007-506047, with partial English translation.
Marzio, L.D. et al, "Apoptotic Effects of Selected Strains of Lactic Acid Bacteria on a Human T Leukemia Cell Line Are Associated With Bacterial Arginine Deiminase and/or Sphingomyelinase Activities," Nutrition and Cancer, 2001, vol. 40, No. 2, pp. 185-196.
Taiwanese Office Action, dated Aug. 5, 2011, for Taiwanese Application No. 095107321.
Watanabe-Fukunaga, R. et al., "Lymphoproliferation disorder in mice explained by defects in Fas antigen that mediates apoptosis," Nature, Mar. 26, 1992, vol. 356, pp. 314-317.

* cited by examiner

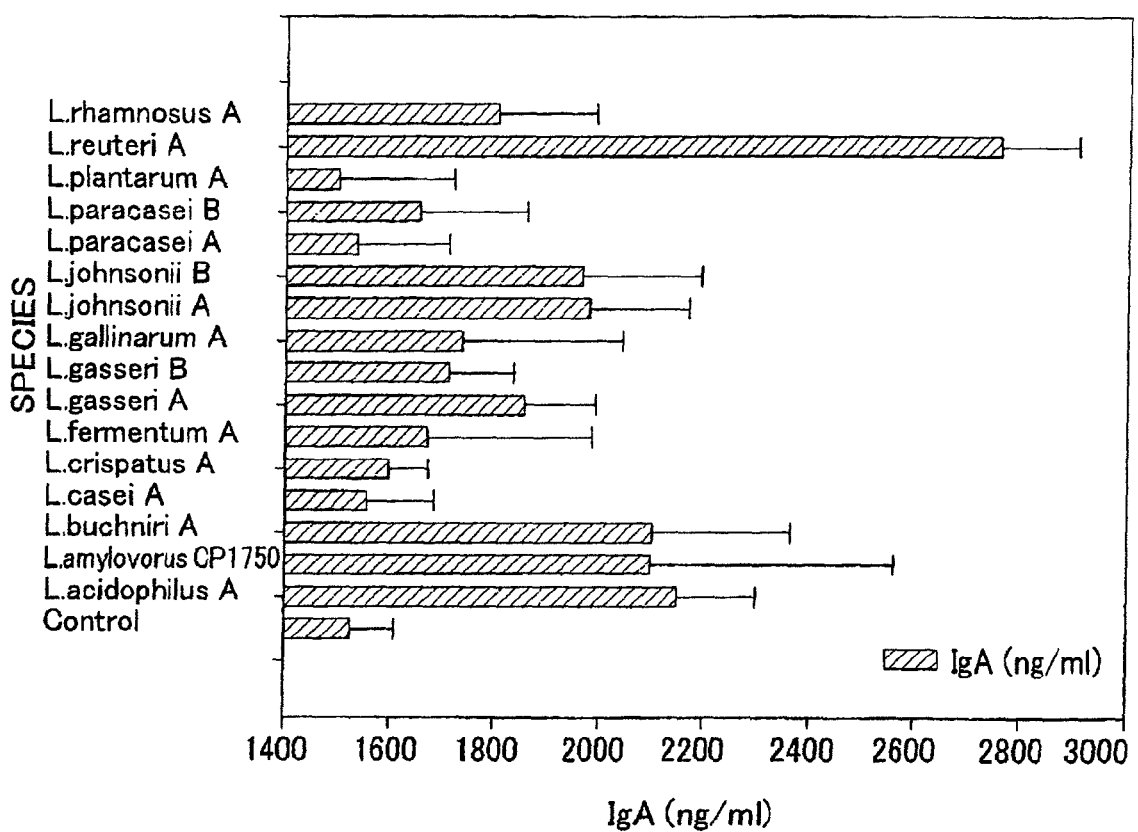

AGENTS FOR PROMOTING IGA PRODUCTION

This application is a Divisional of U.S. application Ser. No. 12/487,978, filed on Jun. 19, 2009, (now abandoned) which is a Continuation of PCT International Application No. PCT/JP2007/074321 filed on Dec. 18, 2007. This application also claims the benefit of priority of Patent Application No. 2006-344233 filed in Japan on Dec. 21, 2006. All of the above are hereby incorporated by reference in their entirety into the present application.

FIELD OF THE INVENTION

The present invention relates to an agent for promoting IgA production. Particularly, the present invention relates to an agent for promoting IgA, which functions effectively in intestine.

BACKGROUND OF THE INVENTION

IgA has been known as a molecule present in saliva, intestine, trachea and the like, which has an important role in enhancing barrier functions of mucosa such as blocking microorganisms and allergen which penetrate through mucosa such as intraoral or intestinal mucosa or the like. Additionally IgA protect an immunologically immature infantile body and it has been well known that IgA from mother's milk is used for immunological compensation as passive immunity.

On the other hand, regarding immunomodulatory functions of lactic acid bacteria, there have recently been several reports and information about mechanisms, and differences among species or strains have been increasingly elicited (Tetsuji Hirota: New Food Industry, Vol. 32, No 10, p 9 (1990)). However, in these reports, not all the immunomodulatory functions were covered and not all species of lactic acid bacteria have been discussed. Thus only insufficient information has been obtained without comprehension of the overview. Lactic acid bacteria which promote secretion of IgA have been partially discussed and particularly bacteria of genus *Bifidobacterium* is considered to have some role in infants, since the abundance ratio thereof in infantile feces is high. There is an attempt of co-culturing *Bifidobacterium* bacteria with Peyer's patch cells to select bacteria with high activity to induce IgA production. Specifically, presence of strains of *Bifidobacterium longum* and *Bifidobacterium breve* having strong promoting activity on IgA secretion were reported (JP 02-280059). However, *Bifidobacterium* bacteria have been known to be present scarcely in human adult intestine, and therefore it is expected that normally they hardly contact Peyer's patch cells. Indeed, such species or strains individually selected have not been confirmed about whether they sufficiently function in human intestine.

Having reviewed lactic acid bacteria in general, there are no reports suggesting relationship between *Lactobacillus* bacteria and IgA production, specifically there are no reports about attempts to compare IgA production-promoting activities among *Lactobacillus* species or strains which are abundant in intestine where Peyer's patch having important role in gut immunity exits and which have high localization in order to find species or strains having high activity. Regarding the intestinal localization of *Lactobacillus* bacteria in human, *Lactobacillus amylovorus* (*L. amylovorus*) was reported to be a lactic acid bacteria belonging to genus *Lactobacillus* which is dominant in human flora as well as *Lactobacillus paracasei*, *Lactobacillus gasseri* and *Lactobacillus johnsonii* (Bioscience Microflora, 22 (3), 75-83, 2003).

SUMMARY OF THE INVENTION

The present invention provides *Lactobacillus* bacteria which promote IgA production by enhancing the function of Peyer's patch or the like and an agent for promoting IgA production comprising the *Lactobacillus* bacterial cells as an active ingredient.

The present inventors demonstrated that there were differences observed in the activity of promoting IgA production among *Lactobacillus* bacteria species by determining activity of promoting IgA production in Peyer's patch for various *Lactobacillus* strains by using various strains which exist or do not exist in human intestinal tract (those of human feces origin or other origin). Particularly among human intestinal tract-fixed *Lactobacillus* bacteria species *Lactobacillus amylovorus* was found to have enhanced activity of inducing IgA production.

Thus, the present invention is an agent for promoting IgA production comprising *Lactobacillus amylovorus* cells as an active ingredient, particularly an agent for promoting IgA production comprising *Lactobacillus amylovorus* CP1750 (FERM BP-10532) as an active ingredient.

According to the present invention an agent for promoting IgA production which may enhance immune barrier. Thus the present invention provides a immunomodulator, a food or feed (including beverage), particularly fermented milk, nutritional food, functional food, food for specified health use, health drink, tablet or the like, for enhancing immune barrier. The agent for promoting IgA production according to the present invention may enhance mucosal barrier function to prevent invasion of food allergens and pathogenic microorganisms as well as environmental allergens such as pollens, mites, house dust and the like.

BRIEF DESCRIPTION OF THE DRAWINGS

FIG. 1 is a comparison between promoting activities on IgA production for different *Lactobacillus* bacteria. Control was PBS without bacterial cells. Bars show standard errors.

DESCRIPTION OF THE PREFERRED EMBODIMENTS

The present invention relates to an agent for promoting IgA production containing *Lactobacillus* bacterial cells which have been unknown about induction potency of IgA which is active for preventing antigenic materials including allergens from contacting mucosa. As used herein an "agent for promoting IgA production" means a composition which has an activity of promoting IgA production. The application of the agent for promoting IgA production of the present invention is not limited as long as the purpose thereof is promoting IgA production and the agent may be used as a medicament or an additive for food (including beverage). Particularly, the agent for promoting IgA production contains as an active ingredient *Lactobacillus amylovorus* cells which was confirmed to have high induction potency of IgA production among *Lactobacillus* cells which are highly localized in intestinal tract and are believed to have abundant opportunity of contacting immunocompetent tissues in intestine. The *Lactobacillus amylovorus* strains which can be used for the present invention include *Lactobacillus amylovorus* CP1750. *Lactobacillus amylovorus* CP1750 was deposited in International Patent Organism Depositary, National Institute of Advanced Industrial Science and Technology (AIST Tsukuba Central6, 1-1, Higashi 1-chome Tsukuba-shi, Ibaraki-ken 305-8536 Japan) and designated to Accession No. FERM BP-10532.

IgA is generally highly produced by mucosal tissues such as Peyer's patch, an IgA is an antibody frequently found in secretory fluids from trachea or intestine, in saliva and in initial mother's milk. Peyer's patch is a tissue which exists in intestinal mucosa of mammals including human and which contains a large amount of IgA-producing cells. The inventors cultured Peyer's patch in the presence of various *Lactobacillus* bacteria which are observed in human intestinal flora or various *Lactobacillus* bacteria which do not or scarcely exist in human intestinal flora, and tested IgA production of the Peyer's patch to demonstrate that there were differences observed in the activity of promoting IgA production, and found that *L.amylovorus* had a particularly high activity of promoting IgA production among *Lactobacillus* species which are dominant in human intestinal flora. It is possible to verify that these *L. amylovorus* strains can be used for the present invention by co-culturing Peyer's patch cells in the presence of various *L.amylovorus* strains.

The activity of promoting IgA production on Peyer's patch cells may be determined as follows. Bacteria, for example *Lactobacillus* bacteria may be cultured in a conventional media and condition, for example, in MRS medium (Difco) at about 37° C.-45° C. for 12-19 hours, recovered by centrifugation and then the obtained cells may be washed with distilled water or an appropriate buffer such as PBS, sterilized by heating at 100° C. (for, for example 10 minutes) to store them for later determination. Peyer's patch cells may be prepared from mouse intestine. Mouse intestine may be placed in a suitable medium for Peyer's patch such as RPMI medium and agitated at about 37° C. for about one hour until the cells are dissociated. The resulting cell suspension may be passed through a mesh to remove undesired debris, and then the resulting cells may be washed with an appropriate medium such as RPMI to obtain a preparation of Peyer's patch cells. The obtained Peyer's patch cells are plated in 96-well plates containing an appropriate medium, for example RPMI medium supplemented with 5% FCS at about $5 \times 10^5$ cells/well, and the aforementioned bacterial cells are added at about 10 µg/ml, and then the plates may be cultured at 37° C. for about 7 days under 5% $CO_2$ atmosphere to obtain supernatant.

IgA amount in the obtained supernatant may be determined by conventional techniques such as ELISA. For example, suitably diluted anti-mouse IgA antibody may be added as a primary antibody to ELISA plate at about 50 µl and the plate may be left standing overnight at 4° C. for coating. The wells are washed with PBS-TWEEN® polysorbate surfactant solution before adding 100 µl of 1% BSA/PBS-TWEEN® polysorbate surfactant solution to each well, and the plates are left standing for 2 hours at a room temperature for blocking. The wells were washed, and 50 µl of a IgA standard or appropriately diluted sample was added to the wells and the plates are left standing for 2 hours at a room temperature. After washing the wells, 50 µl of a secondary antibody, such as biotinylated anti-mouse IgA, diluted with 1% BSA-PBS-TWEEN® polysorbate surfactant solution is added to the wells, and the plates are left standing for 2 hours at a room temperature. After washing the wells with PBS-TWEEN® polysorbate surfactant, 50 µl of alkaline phosphatase solution diluted with 1% BSA/PBS-TWEEN® polysorbate surfactant solution is added to the wells and the plates are left standing for one hour at a room temperature. After washing the wells with PBS-TWEEN® polysorbate surfactant, 50 µl of disodium 4-nitrophenylphosphate dissolved in diethanolamine-HCl buffer to 1 mg/ml was added to the wells to develop to determine the amount of the produced IgA in each well by measuring absorbance at 405 nm.

CP1750 strain (FERM BP-10532), which was determined by such methods and which is superior in the activity of promoting IgA production in Peyer's patch, had specifically high affinity to human intestinal tract and was therefore expected to exhibit very high activity of promoting IgA production in human intestine and was particularly preferable as the active ingredient of the agent for promoting IgA production according to the present invention.

Without wishing to be bound by any theory, the inventors consider that lactic acid bacteria localized in human intestine, particularly *Lactobacillus* species or strains, are superior in total activities including adjuvant activity by promoting IgA production from antibody producing cells in Peyer's patch and further acting nonspecifically on IgA producing cells to enhance IgA production to processing antigens more effectively.

*L.amylovorus* strains which are confirmed to have the activity of promoting IgA production from Peyer's patch, for example CP1750 (FERM BP-10532), may be used as the active ingredient of the agent for promoting IgA production according to the present invention in any form including live cells, killed cells, homogenized cells, cell lysate and powdered cells as long as they do not loss the activity of promoting IgA production. Thus, unless otherwise indicated, "*L.amylovorus* cells" include live cells, killed cells, homogenized cells, cell lysate and powdered cells and any other forms. Particularly cultured live cells and lyophilized cells of *L.amylovorus* cells will be valuable from the viewpoints of convenience. If necessary, the activity of promoting IgA production from Peyer's patch of any of these forms can be verified by the aforementioned methods.

Where the agent for promoting IgA production according to the present invention is used as a medicament, in addition to *L.amylovorus* cells the agent may contains other medicaments and pharmaceutically acceptable conventional excipients and additives. The formulation may be in a form of tablet, powder, pill, granule, capsule, sugar coated tablet or syrup, which may be produced according to conventional methods. The agent for promoting IgA production according to the present invention may be added to various food (including beverage) or feed, particularly fermented milk, nutritional food, functional food, food for specified health use, health drink or tablet. For any of these forms the target intake of the agent for promoting IgA production according to the present invention is 20 mg (dry weight) or more per day as cell weight (dry weight) (about $10^{10}$ cells: the number of cells may be counted by Coulter counter or the like). Alternately, it is preferable to ingest about 100 g per day for fermented milk or fermented broth. Since the active ingredient of the present invention, *L.amylovorus*, is a lactic bacteria present in human small intestine, ingesting a large amount of the agent for promoting IgA production according to the present invention would not cause problematic side effects. The agent for promoting IgA production according to the present invention is therefore suitable for food for human. Namely, the agent for promoting IgA production according to the present invention is suitable for use as food or for adding to food as it is.

Although *L.amylovorus* used in the present invention may be cultured in a medium and culture condition which are well-known by those skilled in the art, for the purpose of producing a preparation for ingestion by human such as a medicament, food or beverage for human, it is preferable to use a medium which is not harmful for human, for example a medium made of only ingredients of food grade.

*L. amylovorus* used in the present invention can be cultured according to culturing conditions and in a medium, which are well known to those skilled in the art. Meanwhile, in order to prepare a preparation to be ingested by human, such as a medicine, food and drink for human, a medium that is not deleterious when ingested by human is preferably used. An example of such a medium is one prepared only from food-grade components. For example, using a semi-synthetic medium (regardless of its type) prepared only from food-grade components, *L. amylovorus* is cultured in a range from 37 to 45° C. for 12 to 18 hours, and centrifuged to recover bacterial cells. Subsequently, the recovered cells are washed with sterilized water by centrifugation (repeatedly washed if necessary) to obtain cells of *L. amylovorus* used as the active ingredient of the agent for promoting IgA production of the present invention can be obtained. The cells thus obtained are frozen directly or frozen with addition of an excipient such as dextrin as appropriate, lyophilizing the cells to obtain a raw material for food containing the living cells. On the other hand, the bacterial cells which are washed with sterilized water and then sterilized by heating are frozen directly or frozen with addition of an excipient such as dextrin as appropriate. Then, by performing freeze-drying or spray-drying, a food raw-material containing the dead cells can be obtained. In the embodiment where the inventions is in the form of the cells themselves or in the form of the cells added into foods, various foods or medicines are preferably prepared such that 20 mg or more (dry weight) of the cells are ingested per day.

On the other hand, fermented milk, fermented broth, or mixed fermented broth can be obtained by adding a culture of *L. amylovorus* cultured in a starter medium into a vegetable juice, fruit juice, wort, rice water, milk or mixed juice thereof at a few percents, for example 3% to 6%, fermenting the mixture at 37° C. to 45° C., and cooling the mixture at a final acid degree of 0.85 or more. A sweetener and/or a flavor may be added to the obtained product as appropriate to adjust the sensory characteristics, and the resultant may be used directly as a chilled food product, or it may be further sterilized to prepare a product having a prolonged shelf life. For such a fermented product, it is preferable that the fermented product be orally ingested in an amount of about 100 g/day. Preferably, about $10^{10}$ cells of *L. amylovorus* are included in 100 g of such a fermented product.

When Peyer's patch cells are cultured with the agent for promoting IgA production according to the present invention, the amount of IgA produced in the culture solution significantly increase (see Example). Generally, the IgA production is frequently observed in mucosal tissue cells, the agent for promoting IgA production according to the present invention is considered to have a function to promote IgA production not only in Peyer's patch cells but also in other mucosal tissues. Accordingly, when the agent for promoting IgA production according to the present invention is orally ingested, IgA production will be systemically promoted in mucosal system as well as in mucosae of the intestinal tracts; moreover, the protective function of the mucosal system is systemically enhanced, and allergens intrusion through mucosae are blocked, generally enabling the suppression of onset of allergies including food allergies. For example, the agent for promoting IgA production according to the present invention promotes intraoral IgA production, thereby suppressing periodontal bacteria, and thus it can be used for improving and preventing periodontal diseases. Since the agent for promoting IgA production according to the present invention has almost no or no side effect, it is extremely safe. Additionally, since the agent for promoting IgA production including cells of CP1750 as the active ingredient has a particularly high affinity for the human intestinal tracts, the activity of promoting IgA production thereof is considered to be particularly high.

EXAMPLES

Example 1

1) Preparation of Lactic Acid Bacterial Cells

The species and strains used are described below:
L.rhamnosus A (*Lactobacillus rhamnosus* Strain A)
L.reuteri A (*Lactobacillus reuteri* Strain A)
L.plantarum A (*Lactobacillus plantarum* Strain A)
L.paracasei A (*Lactobacillus paracasei* Strain A)
L.paracasei B (*Lactobacillus paracasei* Strain B)
L.johnsonii A (*Lactobacillus johnsonii* Strain A)
L.johnsonii B (*Lactobacillus johnsonii* Strain B)
L.galinarum A (*Lactobacillus galinarum* Strain A)
L.gasseri A (*Lactobacillus gasseri* Strain A)
L.gasseri B (*Lactobacillus gasseri* B)
L.fermentum A (*Lactobacillus fermentum* Strain A)
L.crispatus A (*Lactobacillus crispatus* Strain A)
L.buchneri A (*Lactobacillus buchneri* Strain A)
L.amylovorus CP1750 (*Lactobacillus amylovorus* CP1750)
L.acidophilus A (*Lactobacillus acidophilus* Strain A)

*L.amylovorus* CP1750 was a strain which was arbitrarily selected from our standard *L.amylovorus* stock. These *Lactobacillus* species and strains were respectively cultured in 100 ml of MRS medium (Difco Laboratories) at 37° C. for 18 hours, the cells were then washed and freeze-dried. After freeze-drying about $10^{11}$ dried cells (about 100 mg) were obtained for each strains. Aliquots of the freeze-dried cells were suspended in PBS and sterilized by heating at 100° C. for 10 minutes, which were used for the following experiments.

2) Culturing of Peyer's Patch Cells in the Presence of *Lactobacillus* Bacterial Cells Intestines were removed from BALB/c mice and Peyer's patches were excised. Collagenase was dissolved in 5% FCS-RPMI to 1 mg/ml into which the excised Peyer's patches were placed and then agitated at 37° C. for one hour. After the cells were dissociated, the cell suspension was passed through a mesh to remove debris and the cells were washed with RPMI to obtain Peyer's patch cells. The Peyer's patch cells were seeded in 96-well plates containing 5% FCS-RPMI to be $5\times10^5$ cells/well. The cell suspension prepared in 1) was added to be 10 µg/ml (dry weigh of cells), which was cultured in FCS-RPMI at 37° C. under 5% $CO_2$, and after culturing for 7 days the culture supernatant was recovered.

3) Determination of IgA Production from Peyer's Patch Cells

The amount of IgA in the culture supernatant obtained in 3) was determined by ELISA. A primary antibody (goat anti-mouse IgA, Zymed Laboratories) was 1000-fold diluted with 0.1 M Na2HPO4 solution and 50 µl of the antibody solution was added to the ELISA plate and coating was conducted by standing the plate at 4° C. overnight. The wells were washed with PBS-TWEEN® polysorbate surfactant and then 100 µl of 1% BSA/PBS-TWEEN® polysorbate surfactant solution was added to each well and left at a room temperature for 2 hours to block the wells. The wells were washed and then IgA standard (IgA: Purified Mouse Myeloma IgA, Zymed Laboratories) or suitably diluted samples were added to the wells at 50 µl, and left standing at a room temperature for 2 hours. The wells were washed and then 50 µl of a secondary antibody (IgA; biotinylated anti-mouse IgA, clone; C10-1, BD Pharmingen) was added to the wells and left standing at a room temperature for 2 hours. The wells were washed with TWEEN® polysorbate surfactant and then 50 μl of 4-nitrophenyl disodium phosphate (Tokyo Kasei Kougyou) dissolved in diethanolamine-HCl buffer (pH8.9) to be 1 mg/ml was added to develop and absorbance at 405 nm was determined. The amount of produced IgA was shown in a graph using the data for IgA standard as a basis (FIG. 1).

Among the strains which exhibited a relatively high promoting activity on IgA production, L.reuteri A, L.bucvhneri A, L.amyulovorus CP1750, and L.acidophilus A (FIG. 1), L.reuteri A, L.buchnery and L.acidophilus A were the species or strains which are normally not observed in human intestine, while L.amylovorus including Strain CP1750 are shown to be lactic acid bacteria which localized on human intestine and are dominant in human intestinal flora.

4) Bacterial Characteristics of L.amylovorus CP1750

A marketed bacterial identification kit (Api50CH: Biomerieux, Product No. 50307) was used to determine characteristics of L.amylovorus CP1750 for carbohydrate assimilation. The results were shown in Table 1.

TABLE 1

| Carbohydrate | assimilation* |
| --- | --- |
| glycerol | − |
| erythritol | − |
| D-arabinose | − |
| L-arabinose | − |
| ribose | − |
| D-xylose | − |
| L-xylose | − |
| adonitol | − |
| beta-methyl-D-xyloside | − |
| galactose | + |
| glucose | + |
| fructose | + |
| mannose | + |
| sorbose | − |
| rhamnose | − |
| dulcitol | − |
| inositol | − |
| mannitol | − |
| sorbitol | − |
| alpha-methyl-D-mannoside | − |
| alpha-methyl-D-glucoside | − |
| N-acetyl glucosamine | + |
| amygdalin | − |
| arbutin | − |
| esculin | − |
| salicin | − |
| cellobiose | + |
| maltose | + |
| lactose | + |
| melibiose | − |
| saccharose | + |
| trehalose | − |
| inulin | − |
| melezitose | − |
| raffinose | + |
| starch | + |
| glycogen | − |
| xylitol | − |
| gentiobiose | + |
| D-turanose | − |
| D-lyxose | − |
| D-tagatose | − |
| D-fucose | − |
| L-fucose | − |
| D-arabitol | − |
| L-arabitol | − |
| gluconate | − |
| 2-keto-gluconate | − |
| 5-keto-gluconate | − |

*"+" represent positive for assimilation and "−" represents negative for assimilation
L. amylovorus CP1750 exhibited a well growth even at 45° C.

REFERENCES

1. JP 02-280059 A
2. New Food Industry, Vol. 32, No. 10, p 9 (1990)
3. Bioscience Microflora, Vol. 22, No. 3, p 75-83 (2003)

The invention claimed is:

1. A method of treating periodontal diease in a human comprising:
    administrating to a human with periodontal disease an agent comprising Lactobacillus amylovorus cells, as an active ingredient, thereby treating the periodontal disease in the human.

2. The method according to claim 1, wherein the agent is in a form of a food.

3. The method according to claim 1, wherein the agent contains $10^{10}$ cells or more per 20 mg (dry weight) of the agent.

4. The method according to claim 2, wherein the agent contains $10^{10}$ cells or more per 20 mg (dry weight) of the agent.

5. The method according to claim 1, wherein the Lactobacillus amylovorus is Lactobacillus amylovorus CP1750, which is designated as Accession No. FERM BP-10532.

* * * * *